United States Patent [19]

Klenk et al.

[11] 4,117,008
[45] Sep. 26, 1978

[54] PROCESS FOR THE PRODUCTION OF BENZOYL CYANIDE (II)

[75] Inventors: Herbert Klenk; Heribert Offermanns, both of Hanau, Germany

[73] Assignee: Deutsche Gold- und Silber-Scheideanstalt vormals Roessler, Frankfurt am Main, Germany

[21] Appl. No.: 802,945

[22] Filed: Jun. 2, 1977

[30] Foreign Application Priority Data

Sep. 20, 1976 [DE] Fed. Rep. of Germany ........ 2642199

[51] Int. Cl.$^2$ .............................................. C07C 63/06
[52] U.S. Cl. ................................................. 260/545 R
[58] Field of Search ..................................... 260/545 R

[56] References Cited

U.S. PATENT DOCUMENTS 4,069,252  1/1978  Findeisen et al. ............... 260/545 R

OTHER PUBLICATIONS

Erlenmeyer, Liebigs Ann. Chem., vol. 287, pp.302-307 (1895).

Primary Examiner—Gerald A. Schwartz
Attorney, Agent, or Firm—Cushman, Darby & Cushman

[57] ABSTRACT

Benzoyl cyanide is made by reacting benzoic anhydride with an alkali cyanide in an inert organic solvent.

19 Claims, No Drawings

PROCESS FOR THE PRODUCTION OF BENZOYL CYANIDE (II)

BACKGROUND OF THE INVENTION

The invention is directed to a process for the production of benzoyl cyanide by reaction of benzoic anhydride with an alkali metal cyanide. Benzoyl cyanide is an important intermediate product for the production of herbicides.

It is known to produce benzoyl cyanide by the action of more than stoichiometrical amounts of copper (I) cyanide on benzoyl chloride. The reaction is carried out at temperatures up to 80° C. in acetonitrile or benzonitrile or in ether with the addition of more than stoichiometrical amounts of lithium chloride or lithium iodide (Normant et al, Bull. Soc. Chim. France (1972) pages 2402–2403) or at temperatures of 220° to 230° C. in the absence of a solvent (Org. Synth. Coll. 3, 112–114). At best these processes give a yield of 65%.

It is also known to convert benzoyl chloride to benzoyl cyanide by means of an alkali cyanide in a two phase system consisting of water and a solvent which is immiscible with water in the presence of a quaternary alkyl ammonium salt (Koenig, Tetrahedron Letters No. 26 (1974), pages 2275 to 2278). In this process the yield only amounts to 60%.

Furthermore, it is known to produce benzoyl cyanide from benzoyl chloride by reaction with water free hydrogen cyanide and an at least equimolar amount of pyridine (Z. Phys. Chem. 192 (1943), 200–201). This process gives yields of 78%.

A disadvantage of these known processes is that there are formed byproducts to a considerable extent, particularly the dimer of benzoyl cyanide (the benzoyloxyphenyl malonitrile). Consequently, not only is the yield unsatisfactory but also its purity. Benzoyl cyanide can be separated from its dimer only with considerable difficulty and even then only incompletely.

Finally, it is known to produce benzoyl cyanide by reaction of a mixture of benzoic anhydride and potassium cyanide at a temperature of 190° C. (Erlenmeyer, Liebigs Ann. Chem. 287 (1895) 302 et seq., particularly pages 305 to 307). This process merely results in a yield of 10%.

SUMMARY OF THE INVENTION

There has now been found a process for the production of benzoyl cyanide from benzoic anhydride and alkali metal cyanide characterized by carrying out the reaction in an inert organic solvent. According to this process it is possible to recover a pure benzoyl cyanide in a yield of at least 95%.

To carry out the process of the invention, benzoic anhydride is reacted with alkali cyanide, preferably sodium cyanide or potassium cyanide, but there also can be used lithium cyanide. Generally it is suitable to use at least stoichiometrical amount of cyanide. Advantageously there is used about 1.05 to 2.0 equivalents of cyanide, especially 1.05 to 1.5 equivalents of cyanide, per mole of benzoic anhydride.

The reaction of the invention is carried out in an organic solvent which is inert to the reactants. As the solvent there can be used for example ethers, e.g., dioxane, dibutyl ether, dioxolane, ethylene glycol diethyl ether, ethylene glycol dibutyl ether, ethylene glycol dimethyl ether or esters, e.g., alkyl alkanoates such as butyl acetate, propyl acetate, amyl acetate, isobutyl acetate, octyl acetate, ethyl propionate, methyl butyrate, ethyl butyrate or methyl valerate. Especially suitable are hydrocarbons, e.g., aromatic hydrocarbons, such as ethyl benzene, mesitylene, cumene, p-cymene, t-butyl benzene or 1,3,5-triethyl benzene and especially benzene, toluene and xylene or aliphatic hydrocarbons such as ligroin with a boiling range of 90° to 140° C., octane or decane, or cyclic hydrocarbons such as cyclohexane, decalin and tetralin, or halogenated hydrocarbons, particularly chlorinated aromatic or aliphatic hydrocarbons such as chlorobenzene, dichlorobenzene, symmetrical tetrachloroethane, carbon tetrachloride, trichloroethylene, trimethylene bromide, ethylene dibromide. There can also be used mixtures of these solvents.

The amount of solvent to be used depends to a certain extent on the type of solvent. Generally it is suitable to add at least about 100 ml of solvent per mole of benzoic anhydride. Advantageously there is used about 200 to 5000 ml, particularly 300 to 1000 ml, of solvent per mole of benzoic anhydride.

The reaction temperature in a given case depends on the type of solvent. Generally there are used temperatures of about 80° to 200° C., especially 100° to 140° C.

Although the pressure can be selected essentially at random (i.e., it is not critical) in order to use a simple apparatus it is advantageous to use a pressure which does not vary substantially from normal pressure, e.g., to use atmospheric pressure. In many cases because of the presence of volatile substances it can be suitable to use an elevated pressure corresponding to the temperature.

Unless otherwise indicated all parts and percentages are by weight.

The materials employed can comprise, consist essentially of or consist of those set forth.

DESCRIPTION OF THE PREFERRED EMBODIMENTS

EXAMPLE 1

A mixture of 45.2 grams (0.2 mole) of benzoic anhydride, 12.3 grams (0.25 mole) of sodium cyanide and 150 ml of chlorobenzene were held under reflux at the boiling point (about 135° C.) for 4 hours. The mixture was then cooled and filtered off under suction. The residue, which essentially consisted of sodium benzoate was washed with chlorobenzene. The filtrate was brought to dryness at 16 mbar and a temperature up to 90° C. There remained a yellow product which according to the infrared spectral analysis was pure benzoyl cyanide. The yield amounted to 25 grams, corresponding to 96% based on the benzoic anhydride employed.

EXAMPLE 2

The procedure was the same as in Example 1 but instead of chlorobenzene there were added 200 ml of xylene and the reaction was carried out at 125° C. The yield amounted to 25 grams, corresponding to 96%, based on the benzoic anhydride employed.

What is claimed is:

1. A process for the production of benzoyl cyanide comprising reacting benzoic anhydride with an alkali metal cyanide in an inert organic solvent selected from ethers, esters, hydrocarbons, halogenated hydrocarbons and mixtures thereof.

2. A process according to claim 1 wherein the alkali metal cyanide is sodium cyanide or potassium cyanide.

3. A process according to claim 1 wherein the temperature is about 80° to 200° C.

4. A process according to claim 3 wherein the temperature is 100° to 140° C.

5. A process according to claim 1 wherein there are used 1.0 to 2.0 equivalents of cyanide per mole of benzoic anhydride.

6. A process according to claim 5 wherein there are used 1.05 to 1.5 equivalents of cyanide per mole of benzoic anhydride.

7. A process according to claim 1 wherein the inert solvent is a hydrocarbon or halohydrocarbon.

8. A process according to claim 7 wherein the inert solvent is an aromatic hydrocarbon, an aliphatic hydrocarbon, a cycloaliphatic hydrocarbon, a chlorinated aromatic hydrocarbon or a chlorinated aliphatic hydrocarbon.

9. A process according to claim 8 wherein the inert solvent is benzene, toluene, xylene, ethyl benzene, ligroin boiling at about 90° to 140° C., cyclohexane, chlorobenzene, dichlorobenzene, trichloroethylene or tetrachloroethane.

10. A process according to claim 1 wherein the inert solvent is an ether, a carboxylic acid ester, a hydrocarbon or a halohydrocarbon.

11. A process according to claim 10 wherein the solvent is an ether.

12. A process according to claim 11 wherein the ether is dioxane or ethylene glycol diethyl ether.

13. A process according to claim 10 wherein the solvent is a carboxylic acid ester.

14. A process according to claim 13 wherein the ester is an alkyl alkanoate.

15. A process according to claim 1 wherein the alkali metal cyanide is sodium cyanide or potassium cyanide, the temperature is about 80° to 200° C., the solvent is a hydrocarbon or halohydrocarbon and there are used 1.0 to 2.0 equivalents of cyanide per mole of benzoic anhydride.

16. A process according to claim 15 wherein the solvent is chlorobenzene or xylene.

17. A process according to claim 16 wherein the solvent is chlorobenzene, the temperature is about 135° C. and there is used 0.25 mole of cyanide per 0.2 mole of benzoic anhydride.

18. A process according to claim 16 wherein the solvent is xylene and the temperature is 125° C. and there is used 0.25 mole of cyanide per 0.2 mole of benzoic anhydride.

19. A process according to claim 15 wherein the temperature is 100° to 140° C.

* * * * *